(12) United States Patent
Nissan et al.

(10) Patent No.: US 8,888,734 B2
(45) Date of Patent: Nov. 18, 2014

(54) FUNCTIONALLY GRADED MATERIAL TUBE AND METHOD FOR USE OF THE SAME IN IMPLANTATION

(75) Inventors: Oded M. Nissan, Modiin (IL); Oshrit Hertz, Modiin (IL)

(73) Assignee: Alcon Research, Ltd., Fort Worth, TX (US)

(*) Notice: Subject to any disclaimer, the term of this patent is extended or adjusted under 35 U.S.C. 154(b) by 36 days.

(21) Appl. No.: 13/488,816

(22) Filed: Jun. 5, 2012

(65) Prior Publication Data

US 2013/0325024 A1 Dec. 5, 2013

(51) Int. Cl.
*A61M 5/00* (2006.01)

(52) U.S. Cl.
USPC .................................................. 604/9; 604/8

(58) Field of Classification Search
CPC ................................................. A61F 9/00781
USPC ........................................................ 604/8, 9
See application file for complete search history.

(56) References Cited

U.S. PATENT DOCUMENTS

| | | | |
|---|---|---|---|
| 4,554,918 A | 11/1985 | White | |
| 4,936,825 A | 6/1990 | Ungerleider | |
| 5,433,701 A | 7/1995 | Rubinstein | |
| 5,558,629 A | 9/1996 | Baerveldt et al. | |
| 6,050,970 A | 4/2000 | Baerveldt | |
| 6,261,256 B1 | 7/2001 | Ahmed | |
| 6,510,600 B2 | 1/2003 | Yaron et al. | |
| 6,699,211 B2 | 3/2004 | Savage | |
| 7,025,740 B2 | 4/2006 | Ahmed | |
| 7,041,077 B2 | 5/2006 | Shields | |
| 7,473,249 B2 | 1/2009 | Scheller et al. | |
| 7,566,173 B2 | 7/2009 | Auld et al. | |
| 7,670,310 B2 | 3/2010 | Yaron et al. | |
| 8,109,896 B2 | 2/2012 | Nissan et al. | |
| 8,313,454 B2 | 11/2012 | Yaron et al. | |
| 2003/0093084 A1 | 5/2003 | Nissan et al. | |
| 2005/0119737 A1 | 6/2005 | Bene et al. | |
| 2006/0173397 A1* | 8/2006 | Tu et al. ........................ 604/8 |
| 2007/0265602 A1 | 11/2007 | Mordaunt et al. | |
| 2008/0161741 A1* | 7/2008 | Bene et al. ................... 604/9 |
| 2009/0204053 A1 | 8/2009 | Nissan et al. | |
| 2010/0114006 A1 | 5/2010 | Baerveldt | |
| 2010/0185138 A1 | 7/2010 | Yaron et al. | |
| 2010/0274259 A1 | 10/2010 | Yaron et al. | |
| 2010/0331975 A1 | 12/2010 | Nissan et al. | |
| 2011/0077626 A1 | 3/2011 | Baerveldt et al. | |
| 2011/0144627 A1 | 6/2011 | Smith | |
| 2011/0245753 A1 | 10/2011 | Sunalp | |
| 2013/0057821 A1 | 3/2013 | Smith et al. | |

FOREIGN PATENT DOCUMENTS

WO    2013/036314 A2    3/2013

OTHER PUBLICATIONS

International Searching Authority, International Search Report, PCT/US2013/43819, Aug. 30, 2013, 2 pages.
International Searching Authority, Written Opinion of the International Searching Authority, PCT/US2013/43819, Aug. 20, 2013, 5 pages.

* cited by examiner

*Primary Examiner* — Leslie Deak
(74) *Attorney, Agent, or Firm* — Haynes and Boone, LLP (57) ABSTRACT

A device for implantation a patient may include a tubular fiber wall that defines at least one opening and at least one lumen continuous with the one opening and adapted to allow the passage of fluid. The tubular fiber wall typically contains a porosity gradient that is adapted to permit passage of different size substances at different locations along the gradient. In one aspect, a second tubular fiber wall substantially encircling the tubular fiber wall.

20 Claims, 4 Drawing Sheets

FUNCTIONALLY GRADED MATERIAL TUBE AND METHOD FOR USE OF THE SAME IN IMPLANTATION

FIELD OF THE INVENTION

The present disclosure relates generally to a tube made of fibrous material and methods of using the same in surgery to replace or repair tubular anatomical vessels, such as blood or lymph vessels, or to substantially reduce fluid pressure in particular anatomical regions.

Some embodiments of the present disclosure are configured to be used to reduce swelling in the body, such as in cases of edema, hydrocephaly, hydrothorax, hydropericardium, pleural effusin, ascites and/or inflammation.

In some instances, embodiments of the present disclosure are configured to be part of an intraocular implant.

BACKGROUND OF THE RELATED ART

Glaucoma, a type of optic neuropathy, is a group of eye diseases affecting the retina and optic nerve typically resulting from increases in intraocular pressure (IOP) to above normal for prolonged periods of time. Elevation of TOP can be caused by decreased drainage of the aqueous humor relative to its production. An elevated IOP can cause irreversible damage to the optic nerve and retinal fibers thereby resulting in a permanent loss of vision if left untreated.

The aqueous humor, a clear fluid that fills the anterior segment of the eye (the space between the cornea and lens), is continuously produced by the eye's ciliary body and has many protective functions such as inflating the globe of the eye, providing nutrition for the cornea, trabecular meshwork, lens and anterior vitreous, and protecting against contaminants of the eye. The aqueous humor passes out of the anterior chamber (the space between the cornea and iris) through to the trabecular meshwork and the uveoscleral pathways, both of which contribute to the aqueous humor drainage system.

Figure 1:
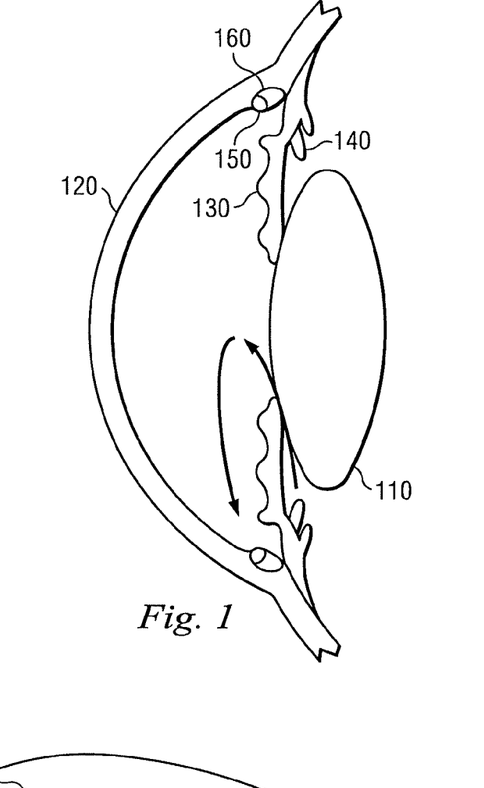
FIG. 1 is a diagram of the front portion of an eye.

FIG. 1 is a diagram of the anterior portion of an eye that helps to explain the processes involved in the development of glaucoma. In FIG. 1, representations of the lens 110, cornea 120, iris 130, ciliary body 140, trabecular meshwork 150, and Schlemm's canal 160 are pictured. Aqueous humor fluid is produced by the ciliary body 140 that lies beneath the iris 130 and adjacent to the lens 110 in the anterior segment of the eye. This aqueous humor bathes the lens 110 and iris 130 and flows to the drainage system located at the base of the cornea 120, in the anterior chamber angle, which extends circumferentially around the eye. The trabecular meshwork 150 extends circumferentially around the anterior chamber and is commonly implicated in glaucoma. The trabecular meshwork 150 limits the outflow of aqueous humor and provides a back pressure that directly relates to IOP. Schlemm's canal 160 is located beyond the trabecular meshwork 150 and is fluidically coupled to collector channels allowing aqueous humor to flow out of the anterior chamber. The two arrows in the anterior segment of FIG. 1 show the flow of aqueous humor from the ciliary bodies 140, over the lens 110, over the iris 130, through the trabecular meshwork 150, and into Schlemm's canal 160 and its collector channels.

One method of treating glaucoma includes implanting a drainage device in a patient's eye. The drainage device allows fluid to flow from the interior chamber of the eye to a drainage area, relieving pressure in the eye and thus lowering IOP. At least a portion of these devices are generally held in place by patches and sutures. In some instances, the device is positioned incorrectly or the device moves out of the correct position which leads to injury to the corneal endothelium (i.e., corneal endothelial touch) and/or erosion of the device. Frequently, fluid filled blebs develop at patches and the drainage area. The development of the bleb typically includes fibrosis, which leads to increased flow resistance and it is generally the case that this resistance increases over time. This development and progression of fibrosis reduces or eliminates flow from the anterior chamber, reducing the capacity of the drainage device to affect IOP.

The system and methods disclosed herein overcome one or more of the deficiencies of the prior art.

SUMMARY

In one exemplary aspect, the present disclosure is directed to device for implantation in a patient. The device includes a tubular fiber wall that defines at least one opening. The device also includes at least one lumen continuous with the at least one opening and adapted to allow passage of fluid therethrough. The tubular fiber wall of the device contains at least one porosity gradient which is adapted to permit passage of different size substances at different locations along the porosity gradient. In one aspect, the tubular fiber wall of the device includes a first region in contact with a surrounding anatomical region when implanted in a patient, and at least a second region in contact with the at least one lumen of the device, wherein the porosity of the tubular fiber wall decreases from the first region to the second region. In a further aspect, the pores within the first region of the tubular fiber wall are sized to enable at least a portion of the cells of the surrounding anatomical region to pass therethrough. In one aspect, the tubular fiber wall includes at least two layers, wherein each layer contains a different porosity gradient. In one aspect, the device is implanted into the eye.

In one aspect, the device further includes at least a second tubular fiber wall substantially encircling the tubular fiber wall. In one aspect, the second tubular fiber wall may contain at least one porosity gradient which is adapted to permit passage of different size substances at different locations along the porosity gradient. In one aspect, the second tubular fiber wall may contain an adhesive.

In another exemplary aspect, the present disclosure is directed to a device for implantation in an eye of a patient. The device includes a tubular member that permits the flow of fluid therethrough and includes a fiber network wherein the fiber network has pores sized and arranged to form at least one porosity gradient and wherein a first end of the tubular member is configured to extend into an anterior chamber of the eye and a second end of the at least a tubular member is configured to extend to a drainage area. In one aspect, the device is held in place by cell ingrowth into the pores of the tubular member. In one aspect, the device further includes a second tubular member.

In another exemplary aspect, the present disclosure is directed to a device for use in treatment of a patient with an ocular condition. The device includes a main portion configured to be implanted in a subconjunctival pocket. The device also includes a tube extending from the main portion and having a length selected to extend from the main portion in the subconjunctival pocket to an anterior chamber of the eye, the tube having a first open end disposable in the anterior chamber and arranged to discharge fluid into a drainage site outside of the anterior chamber, wherein the tube comprises a fiber network that contains pores sized and arranged to form at least one porosity gradient.

In another exemplary aspect, the present disclosure is directed to a method of making a tubular device for implantation in a patient. The method includes dissolving a polymer into a solvent, loading a pump with the dissolved polymer, expelling the polymer solution from the pump, collecting the polymer in a network on a wire wherein the network ultimately contains at least one porosity gradient, and forming the polymer network into a generally tubular shape adapted for implantation into an anatomical region of a patient.

In another exemplary aspect, the present disclosure is directed to a method of reducing fluid pressure in an anatomical region. The method includes providing a tubular shunt having an outer surface and an inner surface, the tubular shunt having at least one porosity gradient between the outer surface of the shunt and the inner surface of the shunt, inserting a first end of the tubular shunt into a relatively higher pressure first region containing fluid, locating a second end of the tubular shunt into a relatively lower pressure second region displaced from the first region, and allowing for passage of fluid from the first region to the second region, thereby reducing fluid pressure in the first region. In one aspect, the method further includes monitoring the fluid pressure within the region where the first end of the tubular shunt is inserted.

In another exemplary aspect, the present disclosure is directed to a method of treating an ocular condition. The method includes providing a tubular shunt having a wall with an inner surface forming a lumen and with an outer surface, the fiber wall having at least one porosity gradient wherein the porosity of the shunt decreases from the outer surface of the shunt toward the inner surface of the shunt in a manner permitting cell-ingrowth into the outer surface, inserting the first end of the tubular shunt into an anterior chamber of an eye, locating the second end of the tubular shunt at a drainage site outside of the anterior chamber, and permitting fluid flow from the anterior chamber to the drainage site. In one aspect, the inner surface of the shunt is substantially impermeable.

It is to be understood that both the foregoing general description and the following detailed description are exemplary and explanatory in nature and are intended to provide an understanding of the present disclosure without limiting the scope of the present disclosure. In that regard, additional aspects, features, and advantages of the present disclosure will be apparent to one skilled in the art from the following detailed description.

BRIEF DESCRIPTION OF THE DRAWINGS

The accompanying drawings illustrate embodiments of the devices and methods disclosed herein and together with the description, serve to explain the principles of the present disclosure.

DETAILED DESCRIPTION

For the purposes of promoting an understanding of the principles of the present disclosure, reference will now be made to the embodiments illustrated in the drawings, and specific language will be used to describe the same. It will nevertheless be understood that no limitation of the scope of the disclosure is intended. Any alterations and further modifications to the described devices, instruments, methods, and any further application of the principles of the present disclosure are fully contemplated as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. For simplicity, in some instances the same reference numbers are used throughout the drawings to refer to the same or like parts.

The present disclosure relates generally to devices and methods for treating a condition where there is swelling or excess fluid in a particular region of the body. In one aspect, the devices and methods may be used to treat glaucoma by relieving elevated intraocular pressure. The devices and methods disclosed herein may enable better positioning, as well as better retention in a particular position, of an implanted tubular device. Additionally, when treating glaucoma, the devices and methods of the present invention may reduce the amount and size of blebs formed in and around implants, thereby reducing the incidence of scar tissue formation and potential further obstruction of fluid flow and damage to the organ, tissue, or region.

Figure 2:
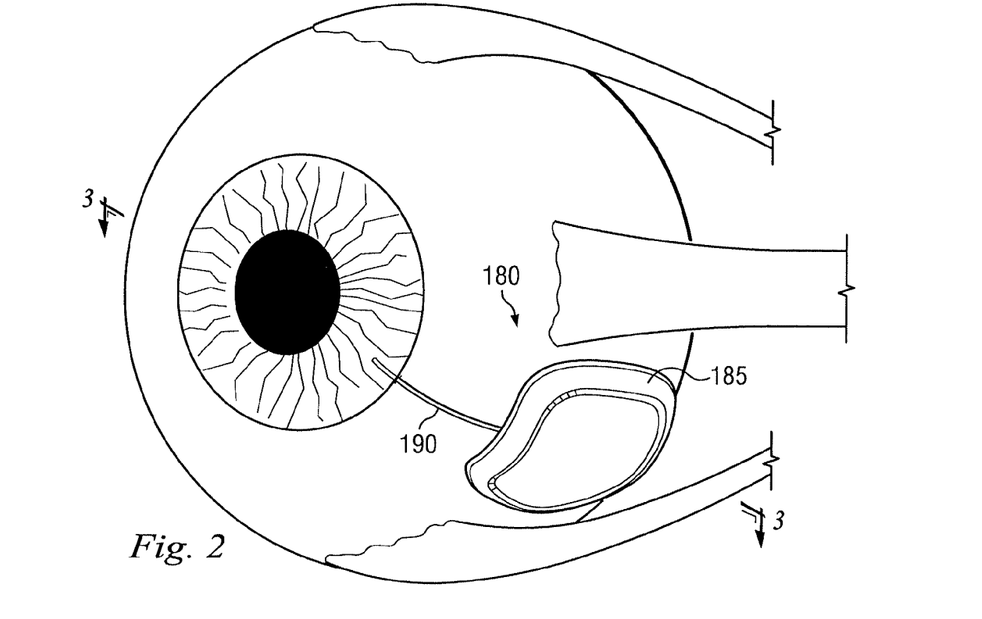
FIG. 2 is an illustration of an exemplary ocular implant in place on an eye according to an exemplary aspect of the present disclosure.
Figure 3:
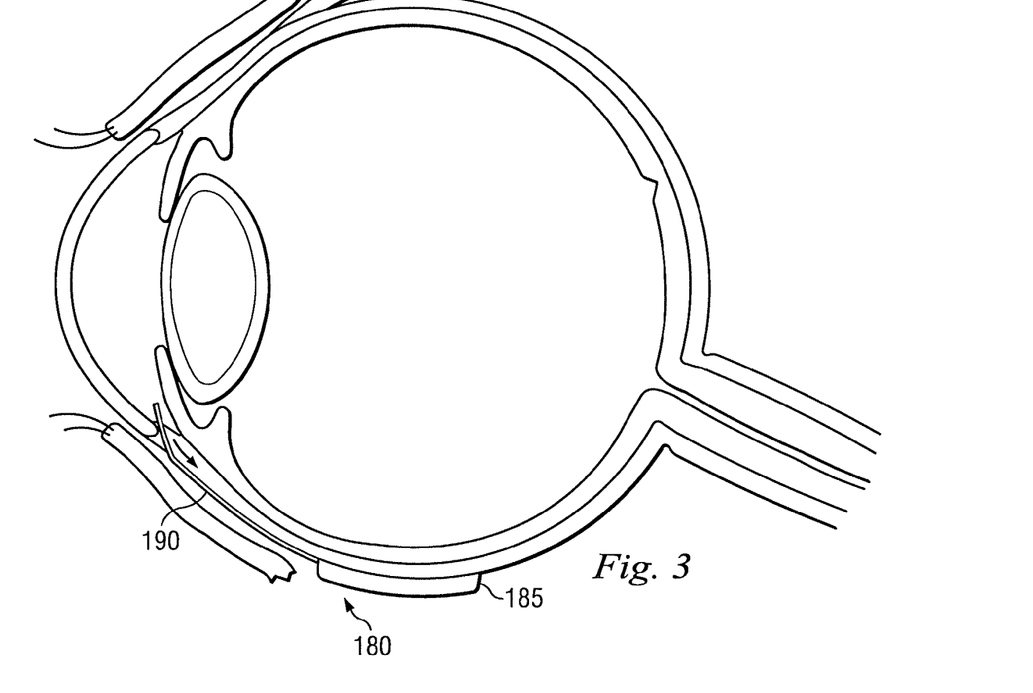
FIG. 3 is a schematic diagram of a cross-sectional view of an eye being treated with the exemplary ocular implant of FIG. 2 according to an exemplary aspect of the present disclosure.

FIGS. 2 and 3 show an exemplary ocular implant 180 inserted into the eye of a patient for the treatment of an eye condition, such as glaucoma, according to one exemplary aspect of the present disclosure. The implant 180 includes a body referred to herein as a plate 185 and includes an implantable tubular device 190 as a drainage tube that extends from the plate 185. The plate 185 may be arranged to carry various components of an IOP control system, and may include a valve, pump, transducers or sensors, a processing system and memory, drug delivery components, a power source or other components that may be used to either control the implant 180 or otherwise treat ocular conditions.

The plate 185 is configured to fit at least partially within the subconjunctival space and is sized for example within a range between about 15 mm (millimeter)×12 mm to about 30 mm×15 mm and has a thickness less than about 2 mm thick and preferably less than about 1 mm thick. The plate 185 may be formed to the radius of the eye globe (about 0.5 inches). It may be rigid and preformed with a curvature suitable to substantially conform to the globe or it may be flexible to conform to the globe. Some embodiments are small enough that conforming to the globe provides little benefit in comfort or implantation technique. The above dimensions are exemplary only, and other sizes and arrangements are contemplated.

When implanted, the plate 185 may be located in the subconjunctival pocket between the conjunctiva and sclera. It may be generally located on an ocular quadrant commonly used for conventional glaucoma drainage devices with plates;

that is, it may be centered such that it is equidistant from the neighboring ocular muscles that define the ocular quadrant chosen for implantation.

The implantable tubular device 190 is sized to bridge the anterior chamber and the plate 185 in the subconjunctival pocket to provide an auxiliary flow path for aqueous humor, bypassing the flow-resistive conventional pathway through the trabecular meshwork and shunting aqueous humor directly to a drainage site. The drainage site or area may be the subconjunctival space, the subscleral space, the subarachnoid space, the supraciliary space, the juxta-uveal space, the choroid, Schlemm's canal, the spiscleral vein, the trabecular meshwork, the uveo-scleral pathway, the collector channel, or a combination thereof. In some embodiments, the tubular device is substantially encircled by an adhesive. The use of the adhesive may alleviate the need to use a patch and/or sutures to maintain the tubular device 190 in place. In a particular embodiment, the adhesive is biodegradable or bioresorbable so that as the adhesive diminishes over time, cell ingrowth into and around the pores of the fiber network of the tubular device 190 is permitted and acts to retain the device in place.

In the example shown, the implantable tubular device 190 is a single tube having a single lumen. Other embodiments include a plurality of implantable tubular devices or a plurality of lumens cooperating together to permit fluid to flow through the implant 180. The implantable tubular device 190 is sized to extend from the plate 185 to the anterior chamber of the eye, as shown in FIG. 3. Aqueous humor may drain through the implantable tubular device 190 from the anterior chamber to and out of the plate 185 to alleviate elevated intraocular pressure conditions.

In conventional systems, the implantable tubular device 190 may have a smooth, dense outer surface and may be held in place or secured on the eye via a patch or sutures. However, the present disclosure is directed to a implantable tubular device that may be secured in place on the eye using alternative arrangements.

Figure 4:
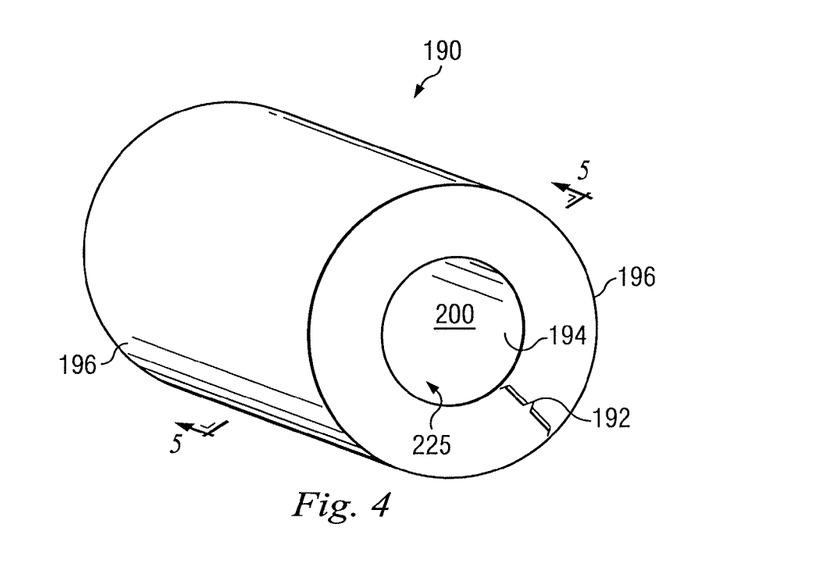
FIG. 4 is an illustration of a portion of an implantable tubular device according to one exemplary aspect of the present disclosure.
Figure 5:
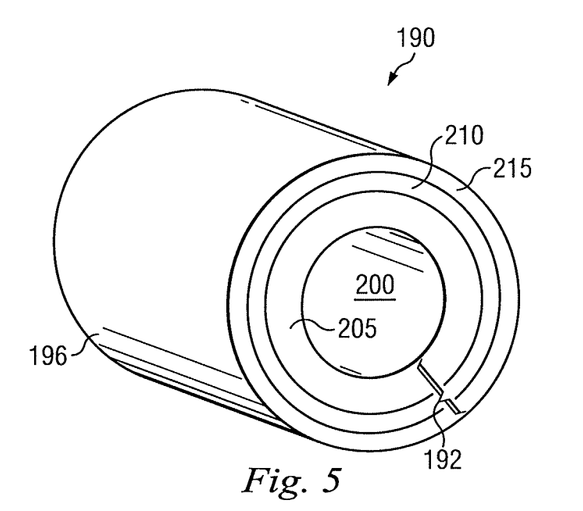
FIG. 5 is an illustration of a cross-sectional view of the implantable tubular device of FIG. 4 taken through the lines 5-5 in FIG. 4, showing additional features according to one exemplary aspect of the present disclosure.

FIGS. 4 and 5 show a portion of the exemplary implantable tubular device 190 in greater detail for the treatment of an ocular condition, including glaucoma. Although described as a treatment device for implantation in the eye, the implantable tubular device may be used anywhere in a patient for the treatment or relief of swelling, fluid retention, or a high pressure condition. Accordingly, it may be implanted independently of the plate 185 and may be sized to provide appropriate relief to a treated condition. FIG. 4 shows a view of an end region and FIG. 5 shows a cross-sectional view taken through the lines 5-5 in FIG. 4. As shown in FIG. 4, the device contains a tubular fiber wall 192 and at least one lumen 200 defined by the tubular fiber wall 192.

The tubular fiber wall 192 has an inner surface 194 facing and defining the at least one lumen 200 and has an outer surface 196 facing outwardly toward the environment or anatomical region into which the device 190 is to be implanted. Other embodiments of the implantable tubular device 190 contain one or more lumens that are not connected with one another and are surrounded by the tubular fiber wall 192.

The tubular fiber wall 192 may be flexible or inflexible based on its expected use in the body of a patient. Here, the tubular fiber wall 192 is cannular, tubelike or vasiform in its overall appearance. In one embodiment, the tubular fiber wall 192 is made of a fiber network.

The tubular fiber wall 192 is typically made of one or more polymers or polymeric materials, biostable materials, biodegradable materials, or a combination thereof. The actual choice of which type of materials to use may readily be made by one of ordinary skill in the art. In some instances, the polymers or polymeric materials can be polyurethanes (including polyurethane dispersions), ethylene vinylacetate polymers, hydrogels such as cross-linked gelatin, detran, polycarboxylic acids, cellulosic polymers, polyvinylpyrrolidone, maleic anhydride polymers, acrylic latex dispersions, polyvinyl alcohols, polyethylene oxides, glycosaminoglycans, polysaccharides, polyesters, polyacrylamides, polyethers, polyvinylidene difluoride (PVDF), polylactic acid (PLA), polyglycolic acid (PGA), polyamide, silicone, or any combination of these materials. In one embodiment, the polymers or polymeric materials include polyvinylidene difluoride (PVDF), polylactic acid (PLA), polyglycolic acid (PGA), polyamide, silicone, or any combination of these materials. The biostable materials may include some or all of the above listed polymers or polymeric materials but are specifically not biodegradable or bioabsorbable. Examples of biostable materials include polyether urethane, silicones, polyamides, such as nylon-66, polyimides, polycarbonates, polyethers, polyesters such as polyethylene terephthalate, polyvinyl aromatics such as polystyrenes, polytetrafluoroethylenes and other classes of fluoropolymers such as poly (ethylene-chloro-trifluoroethylene), fluorinated ethylene-propylene copolymers, perfluoroalkoxy copolymers and fluoroelastomers, polyolefins, such as polyethylenes, polypropylenes, polyisoprenes, and ethylene alpha olefin copolymers, acrylic polymers and copolymers, vinyl halide polymers and copolymers, such as polyvinyl chloride, polyvinyl ethers, such as polyvinyl methyl ether, polyvinyl esters, such as polyvinyl acetate, polyvinyl ketones, polyvinyl halides, such as polyvinylidene fluoride and polyvinylidene chloride, polyacrylonitrile, as well as copolymers of vinyl monomers with each other and olefins, such as ethylene-methyl methacrylate copolymers, acrylonitrile-styrene copolymers, acrylonitrile butadiene styrene (ABS) resins, polysulfones, polyetherimides, polyetheretherketones, polyarylketones, epoxy resins, liquid crystalline polymers, polyphenylene sulfides, polyphenylene oxides, polyamideimides, polyacetals, polyketones, polyarylates, ethylene-vinyl acetate copolymers, and blends of the aforementioned. The biodegradable (or bioabsorbable or bioreabsorbable) materials may include some or all of the above listed polymers or polymeric materials. In some instances, the biodegradable materials include poly(lactic acid)s, poly(glycolic acid)s, poly(lactic-co-glycolic acid)s, polyanhydrides, poly(orthoester)s, poly(hydroxybutyrate)s, poly(hydroxyvalerate)s, polydioxanes, polyphosphazone, polycaprolactones, polyamino acids, collagen, or any combination of these materials. Where a biodegradable material contains a therapeutic agent, the therapeutic agent may elute from the biodegradable material or be released from the polymer as a consequence of degradation. In some instances, the tubular fiber wall 192 is made of about 70% to about 80% polylactic acid and about 20% to about 30% polyglycolic acid. Typically, the tubular fiber wall 192 is made by electrospinning at least one of the above listed materials. The fibers that make up the tubular fiber wall 192 may have any diameter and in some instances have a diameter of about 2 to about 4 micrometers (μm).

The lumen 200 is sized and structurally configured to convey fluid from one site in the patient to another site to relieve swelling, fluid retention, or a high pressure condition. The lumen 200 may have any cross-sectional shape such as, but not limited to, fluted, teardrop, elliptical, airfoil, circular, oval or polygonal. In some embodiments, the lumen 200 is sized to prevent the passage of cells therethrough. In other embodiments, the lumen 200 is sized to allow for the passage of cells therethrough. In one example, if the device 190 is to be used to replace a particular blood vessel, the lumen 200 may be about 25 μm in diameter to permit the passage of red and white blood cells. In some instances, the size of the lumen 200 may restrict what type of cell or biologic material may pass therethrough.

At least one opening 225, labeled in FIG. 4, in the end region of the implantable tubular device 190 provides access to the lumen 200 for the passage of fluid therethrough. The at least one opening 225 may also have any cross-sectional shape, such as fluted, teardrop, elliptical, airfoil, circular, oval or polygonal. The cross-sectional shape of the lumen 200 may be the same as or different than that of the at least one opening 225. In some aspects, the size of the at least one opening 225 prevents or restricts the type or size of cell or biologic material that can pass therethrough. The at least one opening 225 can be adapted to connect to other components of an implant or tools necessary to place the tubular device 190 within a patient. In embodiments having more than one opening 225, the size of the openings can vary from one another so that the tubular device 190 narrows or expands in a particular orientation. In other instances, the lumen 200 and the at least one opening 225 have substantially the same size diameter. In one aspect, where the device 190 is to be implanted into the eye of a glaucoma patient, the implantable tubular device 190 has two openings 225, one at each end, and one lumen 200 connecting the openings, with each opening and the lumen having a diameter of about 180 to about 400 μm. In one aspect, the implantable tubular device 190 has an outer diameter of about 600 μm. In some instances, both the diameter of lumen 200 and the outer diameter can vary along the length of the implantable tubular device 190. The diameter of the lumen 200 and the outer diameter can incrementally increase or decrease along the length of the implantable tubular device 190. In addition, the diameter of the lumen 200 and the outer diameter can increase, decrease or remain the same size along the length of the implantable tubular device 190 independent of each other. For example, the diameter of the lumen can be smaller towards one opening 225 than that near a different opening 225 while the outer diameter remains the same size along the length of the implantable tubular device 190. Thus, the tubular fiber wall 192 would be thinner where the diameter of the lumen 200 is larger. When the device 190 is to be implanted into the eye of a glaucoma patient, the end with the smaller lumen diameter would be implanted into the anterior chamber whereas the end with the larger lumen diameter may collapse and allow for fluid absorption through the tubular fiber wall 192.

The tubular fiber wall 192 may be formed of a single layer or multiple layers depending on the embodiment. In one embodiment, the tubular fiber wall 192 contains a single layer of at least one material with at least one porosity gradient. In an alternative embodiment, the tubular fiber wall 192 contains more than one layer of at least one material with at least one porosity gradient. As best seen in FIG. 5, for example, the tubular fiber wall 192 includes a first layer 205 forming the lumen 200 of the implantable tubular device 190, an optional second layer 210 disposed around the first layer 205, and an optional third layer 215 disposed about the second layer 210.

The first layer 205 may be formed of a polymeric material, a biostable material, a biodegradable material, or any combination thereof, and may be formed with one or more porosity gradients. In this example, the second layer 210 substantially encircles the first layer 205. The second layer 210 may be made of the same, a similar or a different material than the first layer 205. The second layer 210 may be formed with the same, similar or different amount and/or type of porosity gradient(s). In this example, the third layer 215 substantially encircles the second layer 210. The third layer 215 may be made of the same, a similar or a different material than the first layer 205 and/or the second layer 210. The third layer 215 may also be formed with the same, a similar or a different amount and/or type of porosity gradient(s).

Although shown in FIG. 5 with three layers, the tubular fiber wall 192 may contain any number of layers. In some instances, the number of layers of the tubular fiber wall 192 is dependent on the size and/or type of implant and/or the function the implant will perform. In some aspects, each layer is comprised of a different polymeric material. In some instances, the layers are made of the same material but contain different porosity gradients. In other instances, the layers are made of different materials but contain the same or similar porosity gradients. Depending on the embodiment, the layers can vary in thickness and length.

Figure 6:
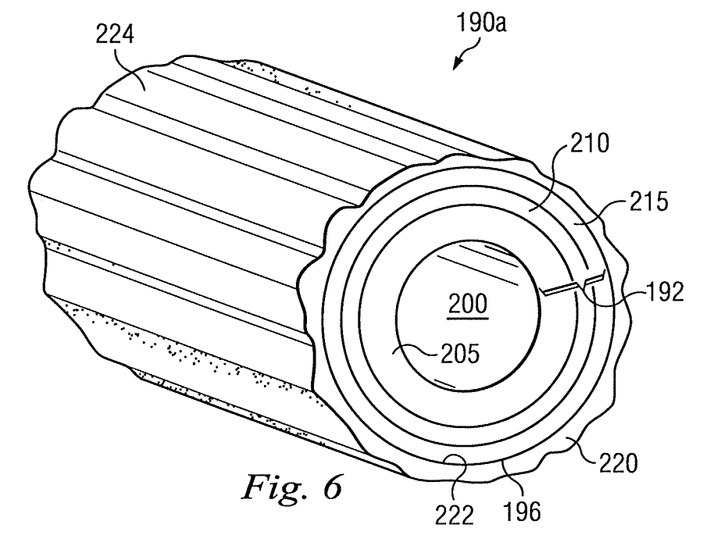
FIG. 6 is an illustration of a cross-sectional view of an implantable tubular device according to one exemplary aspect of the present disclosure.

While the implantable tubular device 190 includes a tubular wall 192 formed of three layers, the implantable tubular device 190 may contain additional tubular walls. FIG. 6 shows an embodiment of an implantable tubular device, referenced herein as 190a, having a second tubular wall 220 formed about the first tubular fiber wall 192. Referring to FIG. 6, the second tubular wall 220 includes an inner surface 222 and an outer surface 224. In this case, the inner surface 222 contacts the outer surface 196 of the outermost layer 215 of the tubular fiber wall 192. Accordingly, the outer surface 224 of the second tubular wall 220 contacts a surrounding anatomical region when the device 190a is implanted in a patient.

In the embodiment shown, the second tubular wall 220 substantially encircles or surrounds the outermost layer (i.e., 215 in FIGS. 5 and 6) of the tubular fiber wall 192. However, in other embodiments, the second tubular wall 220 only partially surrounds the tubular fiber wall 192. For example, the second tubular wall 220 may encircle only about 50%, about 60%, about 70%, or about 80% of the tubular fiber wall 192. In some instances, the second tubular wall may encircle about 90%, about 95%, about 96%, about 97%, about 98%, about 99% or, in some instances, about 100% of the tubular fiber wall 192. The second tubular wall 220 may be made of the same, a similar or a different material than any of the layers 205, 210, 215 of the tubular fiber wall 192. In one aspect, the tubular fiber wall 192 and the second tubular wall 220 are made of the same polymeric material. The porosity of the second tubular wall 220 and the tubular fiber wall 192 may be continuous, i.e., the porosity may increase or decrease across the walls, without any steps or gradations in porosity. In contrast, the connection between the second tubular wall 220 and the tubular fiber wall 192 may provide an incremental increase or decrease step in porosity.

In some instances, the second tubular wall 220 may be made of a different material than the tubular fiber wall 192. For example, the second tubular wall 220 may be made of a non-fiber construct. In one example, the tubular fiber wall 192 may be made of a polymeric material while the second tubular wall 220 may be made of an adhesive. In this embodiment, the adhesive binds or reversibly binds to the surrounding anatomical region securing or reversibly securing the implantable tubular device 190 in place.

In this embodiment, the adhesive forming the second tubular wall 220 may be any suitable biological adhesive including, for example, a biologic glue, a biodegradable polymer (such as those listed above for the tubular fiber wall 192), a bioresorbable material, or a combination thereof. In one aspect of the invention, the biodegradable polymer is polylactic acid, polyglycolic acid, polyhylauronic acid, polyhydroxy acid, hydroxybutanoic acid, cellulose, gelatine, collagen, or a combination thereof. In another aspect, the biologic glue may be made of fibrin, fibrinogen, thrombin, liposome, or a combination thereof. Where a biodegradable or bioresorbable material contains a therapeutic agent, the therapeutic agent may elute from the biodegradable material or be released from the polymer as a consequence of degradation.

The adhesive of the second tubular wall 220 may secure the implantable device 190 in the appropriate location over a period of hours, days, weeks or, in some instances, months. As the biodegradable or bioresorbable second tubular wall 220 degrades over time, cell ingrowth into the tubular fiber wall 192 may occur. Thus, the temporary adhesive of the second tubular wall 220 is replaced at least in part by more permanent cell growth into the tubular fiber wall 192. The ingrowth of cells may permit the implantable tubular device 190 to remain in place for a period of days, weeks, months, and in some instances, years. This manner of maintaining the implantable tubular device 190 in a particular anatomical area or location may decrease the use of and/or need for sutures and/or patches placed over the implanted tubular device 190.

The tubular fiber wall 192 contains pores, i.e., empty or void spaces, that help form at least one porosity gradient. Porosity can be determined by any measurement as would be known to one of ordinary skill in the art. For example, porosity can be expressed as a fraction (or percentage) of the volume of the pores over the total volume of the region. A porosity gradient is a change in porosity from one region of the tubular fiber wall to another region. The porosity (and the resulting porosity gradient) can be determined or created by varying the size of the pores in the tubular fiber wall, the amount of pores in the tubular fiber wall, the density of the fibers of the tubular fiber wall, or a combination thereof. Typically, as the density of the fibers increases, the porosity of the tubular fiber wall decreases. In a porosity gradient, the flow of fluid is permitted to increase or decrease, depending on the size and/or orientation of the pores. In some porosity gradients, the passage of some biologic material, such as cells, is restricted or allowed along certain portions of the porosity gradient. In some instances, the average pore size is small enough to block cell migration into the tubular fiber wall 192 or cell growth (i.e., the increase in cell size) from occurring. The second layer 210 may form a continual porosity gradient with the first layer 205. In one example, porosity is minimized near the lumen 200 to provide suitable conveyance of fluid from a particular site, while porosity is maximized toward the outer surface 196 to permit securing tissue ingrowth to stabilize the implantable device 190 in place. In another example, porosity is maximized near the lumen 200 and minimized near the outer surface 196. In this manner the implantable tubular device 190 may itself serve as a drainage site. In this example, it is beneficial if the pores in the area near the lumen 200 are sized and/or localized within the tubular fiber wall 192 so as to be able to prevent the ingrowth of cells, and still result in a greater porosity than that of the region near the outer surface 196.

Depending on the embodiment, the porosity gradient may increase or decrease in a linear, non-linear, step-wise or graded fashion. The porosity gradient can be continuous and scale up or down to a desired amount, or the porosity gradient can include differing porosity regions (e.g., a region containing 70% porosity can transition to a region containing 40% porosity which can then transition to a region containing 80% or up to 100% porosity). The transitions between the porosity regions can be continuous or abrupt. Likewise the pore distribution throughout the tubular fiber wall may be uniform or varied along the porosity gradient.

A porosity gradient can be found along any direction within the tubular fiber wall. For example, the porosity gradient can extend from one side of the tubular fiber wall to the other side, along any axis. For example, the porosity gradient can extend from the outer surface 196 of the tubular fiber wall (or first region in contact with a surrounding anatomical region when implanted in a patient) to the inner surface 194 (or second region forming the at least one lumen 200) of the tubular fiber wall 192, or vice versa.

Figure 7:
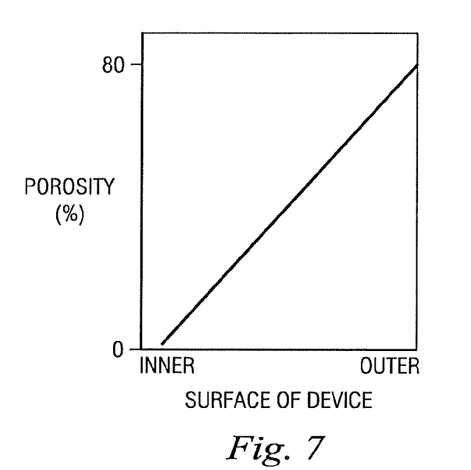
FIGS. 7-9 are graphs showing exemplary porosity gradients that may be found in different embodiments of implantable tubular devices according to exemplary aspects of the present disclosure.
Figure 8:
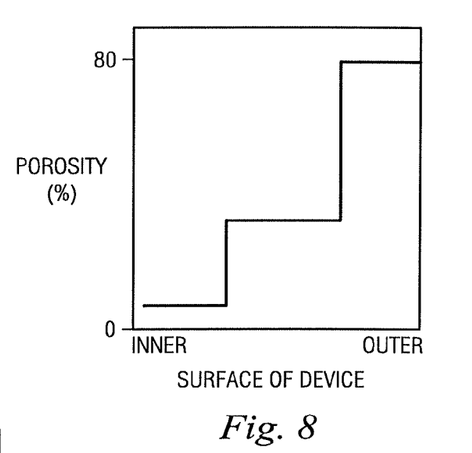
Figure 9:
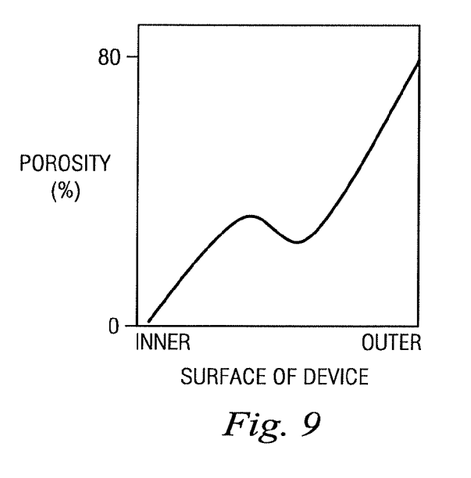

FIGS. 7-9 are graphs demonstrating exemplary porosity gradients between the inner surface 194 and the outer surface 196 of the tubular fiber wall 192. FIG. 7 depicts a graph that demonstrates one example of a linear increase in porosity from about 0% to about 80% as the surface of the tubular fiber wall is changed from the inner surface 194 to the outer surface 196. FIG. 8 depicts a graph that demonstrates one example of a step-wise increase in porosity as the surface of the tubular fiber wall is changed from the inner surface 194 to the outer surface 196. FIG. 9 depicts a graph that demonstrates a non-linear increase in porosity as the distance from the inner surface 194 increases. In an example, the porosity of the first region is about 50% to about 100% porous and the porosity of the second region is about 0% to about 49% porous. Other gradients are contemplated and may be selected based on the particular application, including the propensity for cell growth at the implantation site. In some aspects the porosity range may be up to about 100% porosity. In some aspects of the disclosure, the porosity gradient can extend from one side of the tubular fiber wall a portion of the way to the other side. The porous nature of the outer surface 196 of the first tubular fiber wall 192, allows cell ingrowth into the tubular fiber wall 192. In this manner, the device 190 may be kept in place over time. In one aspect, where the device 190 is to be implanted into the eye of a glaucoma patient, the porosity of the outer surface 196 should be about 60% to about 80% porous. This would allow for cell ingrowth but prevent passage of cells directly therethrough. In another aspect of the invention, the lumen 200 is sized to allow cells therethrough and the pores near the lumen 200, or in the second region, are sized to allow for cell ingrowth into the tubular fiber wall 192.

Some aspects of the disclosure are directed to methods of making an implantable tubular device, as described above, for implantation in a patient. The method of making the implantable tubular device can include electrospinning or extrusion techniques, for example. The method of making the implantable tubular device can include dissolving one or more of the above-listed polymers into a solvent, loading a pump or syringe with the dissolved polymer solution, expelling the polymer from the pump or syringe, typically by application of an electrical charge to the solution, collecting the polymer in a network arrangement on a wire wherein the network ultimately contains at least one porosity gradient, and forming the polymer network into a generally tubular shape adapted for implantation into an anatomical region of a patient. In some instances, the collection of the polymer and the forming of the polymer network into a generally tubular shape occurs substantially simultaneously. Typically the following parameters can be modified or accounted for when designing the resulting polymer network and porosity gradient: molecular weight of the polymer(s), molecular architecture of the polymer(s) (i.e., whether branched, linear, etc.), solution properties such as viscosity, conductivity, and surface tension, electric potential and/or potential gradient, flow rate of the polymer solution, temperature of the polymer solution, concentration of the polymer solution, distance between the pump or syringe and the collecting wire, ambient conditions such as temperature, humidity, and air flow, motion of the collecting wire, size of the opening of the pump or syringe, the angular velocity and diameter of a electrospinning system mandrel collector, distance from a electrospinning system nozzle, nozzle diameter, number and distribution of nozzles, presence or absence of an electrospinning system background collector. In some embodiments, the at least one porosity gradient is dependent on the density of the polymer network.

Some aspects of the invention are directed to a method of reducing fluid pressure in at least one anatomical region, such as those regions affected by glaucoma, edema, hydrocephaly, hydrothorax, hydropericardium, pleural effusin, ascites and/or inflammation. The method includes providing a tubular member or tubular shunt having at least one porosity gradient between the outer surface of the shunt and the inner surface of the shunt. The inner surface of the tubular shunt typically forms a lumen. The method also includes inserting a first end of the tubular shunt into a first anatomical region containing fluid and inserting a second end of the tubular shunt into a second anatomical region distal from the first anatomical region and allowing for the passage of fluid from the first to the second region, which reduces the fluid pressure in the first region. In some instances the fluid pressure within the first anatomical region is monitored. Monitoring the fluid pressure can aid in alleviating pressure build-up or in preventing pressure from dropping too low. For instance, the device may contain a valve which can automatically respond to fluid pressure deviations that are outside of desired fluid pressure ranges or fluid pressure deviations that are too slow or too rapid by opening or closing. The valve may be reversible, i.e., allow for fluid flow in either direction. The valve may open or close partially to allow for a gradual flow of fluid. In some embodiments, the fluid flow is dictated by the differential fluid pressure differences between the ends of the tubular shunt. In other embodiments, suctioning is applied via the tubular shunt to further reduce fluid pressure. In some aspects of the method, a drug can be applied through at least a portion of the shunt to further reduce fluid pressure in the first anatomical region. The tubular shunt may remain in place for a period of days, weeks, months, and in some instances, years. The location of the tubular shunt may be monitored over time to ensure proper placement within the region it was implanted.

In some embodiments, the fluid pressure is reduced in the anterior chamber of the eye by inserting one end of the tubular shunt, formed at least in part by the implantable tubular device 190, into the anterior chamber and another end of the tubular shunt into a drainage site outside of the anterior chamber. In some instances, the inner surface of the shunt (typically facing the lumen) is impermeable to biologic material such as cells and fluids. The fluid pressure within the anterior chamber may be monitored over time after implantation of the tubular shunt. The outer surface of the shunt, comprising the tubular fiber wall may contain pores sized and arranged to permit the ingrowth of surrounding cells. Some embodiments include an adhesive on the outer surface of the shunt. When the tubular shunt is implanted in the eye, the shunt may be maintained in place at least initially by the adhesive. Over time, cell or tissue ingrowth into the shunt secures the shunt in place in the eye. Therefore, even as the adhesive degrades, the shunt may become more particularly secured in place through cell ingrowth. Accordingly, the need to suture a patch or to otherwise anchor the shunt in place decreases. In one exemplary aspect, the shunt, comprising the implantable tubular device 190 is initially secured in place using a patch and sutures. However, after a period of time, because of the cell-ingrowth into the porous walls of the shunt, the patch and sutures may be removed, leaving the shunt secured in the eye only by the tissue ingrowth. This may be more comfortable to a patient, may require fewer checkups, and may provide a better clinical result. In some aspects of the method, a drug can be applied through at least a portion of the shunt into the anterior chamber to treat glaucoma. The delivery of the drug and the flow of fluid from the anterior chamber into the drainage site may occur substantially simultaneously.

In some embodiments, a device for implantation in a patient may include a tubular fiber wall that defines at least one opening and at least one lumen continuous with the at least one opening and adapted to allow passage of fluid therethrough. The tubular fiber wall may contain at least one porosity gradient which is adapted to permit passage of different size substances at different locations along the porosity gradient. In some embodiments, the adhesive may be selected from the group consisting of: a biologic glue, a biodegradable polymer, a bioresorbable material, or a combination thereof. In some embodiments, the biodegradable polymer may be selected from the group consisting of: polylactic acid, polyglycolic acid, polyhylauronic acid, polyhydroxy acid, hydroxybutanoic acid, cellulose, gelatine, collagen, or a combination thereof. In some embodiments, the biologic glue comprises: fibrin, fibrinogen, thrombin, liposome, or a combination thereof. In some embodiments, the tubular fiber wall comprises a first region in contact with a surrounding anatomical region when implanted in a patient and at least a second region in contact with the at least one lumen of the device. In some embodiments, the porosity of the tubular fiber wall decreases from the first region to the second region. In some embodiments, the first region is about 50% to about 100% porous. In some embodiments, the second region is about 0% to about 49% porous. In some embodiments, the pores within the first region of the tubular fiber wall are sized to enable at least a portion of the cells of the surrounding anatomical region to pass therethrough. In some embodiments, the device is implanted into the eye. In some embodiments, the porosity gradient is created by varying the size of the pores in the tubular fiber wall, the amount of the pores in the tubular fiber wall, the density of the fibers of the tubular fiber wall, the thickness of the tubular fiber wall, or a combination thereof. In some embodiments, the tubular fiber wall comprises at least two layers, wherein each layer contains a different porosity gradient. In some embodiments, each layer is comprised of a different polymeric material. In some embodiments, the device may be implanted in a patient who has glaucoma.

In some embodiments, a method of reducing fluid pressure in an anatomical region may include providing a tubular shunt having an outer surface and an inner surface, the tubular shunt having at least one porosity gradient between the outer surface of the shunt and the inner surface of the shunt. The method may further include inserting a first end of the tubular shunt into a relatively higher pressure first region containing fluid. The method may further include locating a second end of the tubular shunt into a relatively lower pressure second region displaced from the first region, and allowing passage of fluid from the first region to the second region, thereby reducing fluid pressure in the first region. In some embodiments, the method may further include monitoring the fluid pressure within the region where the first end of the tubular shunt is inserted. In some embodiments, the method may further include allowing the tubular shunt to remain implanted in the tissue for a period of months to years. In some embodiments, the method may further include applying a drug through at least a portion of the shunt to further reduce fluid pressure. In some embodiments, the anatomical region is the anterior chamber of the eye. In some embodiments, the method may further include applying suction to the tubular shunt to further reduce fluid pressure. In some embodiments, the inner surface of the shunt is substantially impermeable. In some embodiments, the outer surface of the shunt has pores sized and arranged to permit ingrowth of surrounding cells.

For purposes of the present invention, the following terms are defined below:

In accordance with long standing patent law convention, the words "a" and "an" when used in this application, including the claims, denotes "one or more."

As used herein, the term "about" should generally be understood to refer to both numbers in a range of numerals. For example, "about 1 to 10" should be understood as "about 1 to about 10." Moreover, all numerical ranges herein should be understood to include each whole integer within the range, as well as each tenth.

As used herein, the term "biodegradable" refers to those materials that dissipate over a period of time (i.e., a period of days, weeks, and in some instances, months) upon exposure to bodily fluids, tissues, and the like. This can occur by any method such as dissolution, degradation, absorption and/or excretion.

As used herein, the term "biostable" refers to a material's chemical and physical stability during implantation in living tissue. More specifically, it refers to those materials that do undergo significant degradation upon prolonged exposure (i.e., up to six months, a year, or longer) to bodily fluids, tissues, and the like.

As used herein, the term "patient" refers to any organism into which the device of the present disclosure can be implanted and/or the method of the present disclosure can be practiced on. In certain aspects, the patient will be a vertebrate animal, which is intended to denote any animal species (e.g., a mammalian species such as a human being). In certain embodiments, a "patient" refers to any animal, including but not limited to, human and non-human primates, avians, reptiles, amphibians, bovines, canines, caprines, cavines, corvines, epines, equines, felines, hircines, lapines, leporines, lupines, murines, ovines, porcines, racines, vulpines, and the like, including, without limitation, domesticated livestock, herding or migratory animals or birds, exotics or zoological specimens, as well as companion animals, pets, and any animal under the care of a veterinary practitioner.

The term "substantially" as used herein, typically means to a great or greater degree or extent. In some embodiments, "substantially encircling" means surrounding something at least 50% of the way around the circumference of the object. In some embodiments, it means surrounding something at least 60%, at least 70%, at least 80%, at least 90%, at least 95%, at least 96%, at least 97%, at least 98%, at least 99%, or 100% of the way around the circumference of the object. In some embodiments, "substantially simultaneously" means occurring at or close to the same time.

Persons of ordinary skill in the art will appreciate that the embodiments encompassed by the present disclosure are not limited to the particular exemplary embodiments described above. In that regard, although illustrative embodiments have been shown and described, a wide range of modification, change, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure.

We claim:

1. A device for implantation in an eye of a patient, comprising:
   a tubular member that permits flow of fluid therethrough and is comprised of a fiber network;
   wherein the fiber network has pores sized and arranged to form at least one continuous porosity gradient, wherein the porosity gradient changes, along a radius of the tubular member, from an outer tubular surface of the tubular member to an inner tubular surface of the tubular member, the outer tubular surface being more porous than the inner tubular surface and the outer tubular surface configured to contact eye tissue and permit cell ingrowth, and
   wherein a first end of the tubular member is configured to extend into an anterior chamber of the eye and a second end of the tubular member is configured to extend towards a drainage area.

2. The device for implantation in an eye of a patient of claim 1, further comprising at least a first pressure sensor in fluid communication with the anterior chamber.

3. The device for implantation in an eye of a patient of claim 1, further comprising at least one pump operably connected to the tubular member.

4. The device for implantation in an eye of a patient of claim 1, wherein the drainage area is a subconjunctival space, a subscleral space, a subarachnoid space, a supraciliary space, a juxta-uveal space, a choroid, Schlemm's canal, a spiscleral vein, a trabecular meshwork, a uveo-scleral pathway, a collector channel, or a combination thereof.

5. The device for implantation in an eye of a patient of claim 1, wherein the tubular member is substantially encircled by an adhesive.

6. The device for implantation in an eye of a patient of claim 1, wherein the fiber network comprises at least an outer layer and an inner layer, wherein each of the outer layer and inner layer contains a different porosity gradient.

7. The device for implantation in an eye of a patient of claim 1, wherein the device is held in place by cell ingrowth into the pores of the tubular member.

8. The device for implantation in an eye of a patient of claim 1, wherein the device is initially held in place by a biodegradable adhesive that degrades as cells grow into and around the pores of the fiber network.

9. The device for implantation in a patient of claim 1, wherein the tubular member comprises: a polymeric material, a biostable material, a biodegradable material, a bioresorbable material, or a combination thereof.

10. The device for implantation in a patient of claim 9, wherein the polymeric material comprises: polyvinylidene difluoride (PVDF), polylactic acid (PLA), polyglycolic acid (PGA), polyamide, silicone, or any combination thereof.

11. The device for implantation in a patient of claim 1, wherein the tubular member is a first tubular member and wherein the device further comprises at least a second tubular wall substantially encircling the tubular fiber wall.

12. The device for implantation in a patient of claim 11, wherein the second tubular member contains at least one porosity gradient for permitting passage of different size substances at different locations along the porosity gradient.

13. The device for implantation in a patient of claim 12, wherein the first tubular member and the second tubular member comprise the same polymeric material.

14. The device for implantation in a patient of claim 11, wherein the second tubular member comprises an adhesive.

15. The device of claim 1, wherein the porosity gradient changes along direction perpendicular to a center line of the tubular member.

16. A method of treating an ocular condition, comprising:
   providing a tubular shunt having a fiber wall with an inner surface forming a lumen and with an outer surface, the fiber wall having at least one continuous porosity gradient wherein the porosity of the shunt decreases, along a radius of the tubular shunt, from the outer surface of the shunt toward the inner surface of the shunt in a manner permitting cell-ingrowth into the outer surface;
   inserting a first end of the tubular shunt into an anterior chamber of an eye;
   locating the second end of the tubular shunt at a drainage site outside of the anterior chamber; and permitting fluid flow from the anterior chamber to the drainage site.

17. The method of claim 16, further comprising delivering a drug into the anterior chamber from the tubular shunt for treatment of glaucoma.

18. The method of claim 17, wherein the permitting fluid flow from the anterior chamber to the drainage site and delivering a drug into the anterior chamber for the treatment of glaucoma occurs substantially simultaneously.

19. The method of claim 16, further comprising monitoring location of the tubular shunt over time.

20. The method of claim 16, further comprising monitoring fluid pressure in the anterior chamber over time.

\* \* \* \* \*